(12) United States Patent
Ferritto Crespo et al.

(10) Patent No.: US 7,321,056 B2
(45) Date of Patent: Jan. 22, 2008

(54) SELECTIVE PEROXISOME PROLIFERATOR ACTIVATED RECEPTOR MODULATORS

(75) Inventors: Rafael Ferritto Crespo, Alcobendas (ES); Maria Dolores Martin-Ortega Finger, Alcobendas (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/596,256

(22) PCT Filed: Dec. 8, 2004

(86) PCT No.: PCT/US2004/038232

§ 371 (c)(1),
(2), (4) Date: Jun. 7, 2006

(87) PCT Pub. No.: WO2005/061441

PCT Pub. Date: Jul. 7, 2005

(65) Prior Publication Data

US 2007/0066683 A1    Mar. 22, 2007

Related U.S. Application Data

(60) Provisional application No. 60/550,636, filed on Mar. 5, 2004.

(30) Foreign Application Priority Data

Dec. 15, 2003    (EP) .................................. 03380288

(51) Int. Cl.
*C07C 229/00*    (2006.01)

(52) U.S. Cl. ...................... 562/450; 514/563

(58) Field of Classification Search ................ 562/450; 514/563

See application file for complete search history.

(56) References Cited

U.S. PATENT DOCUMENTS

| 6,294,580 B1 | 9/2001 | Willson et al. |
| 2005/0171204 A1* | 8/2005 | Lindstedt et al. ........... 514/563 |

FOREIGN PATENT DOCUMENTS

WO    WO 03/051821 A    6/2003

* cited by examiner

*Primary Examiner*—Yvonne Eyler
*Assistant Examiner*—Sudhakar Katakam
(74) *Attorney, Agent, or Firm*—MaCharri Vorndran-Jones

(57) ABSTRACT

The present invention is directed to a novel compound, its composition and use of a compound having a structural formula (I), or a pharmaceutically acceptable salt, solvate, hydrate or stereoisomers thereof, which is useful in treating or preventing disorders mediated by a peroxisome proliferator activated receptor (PPAR) such as syndrome X, type II diabetes, hyperglycemia, hyperlipidemia, obesity, coagaulopathy, hypertension, arteriosclerosis, and other disorders related to syndrome X and cardiovascular diseases

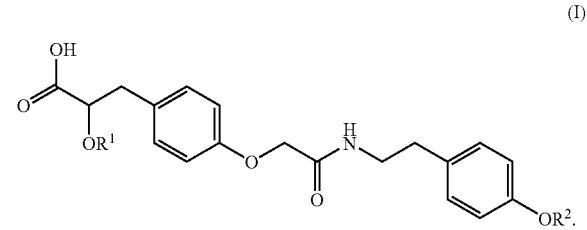

(I)

11 Claims, No Drawings

SELECTIVE PEROXISOME PROLIFERATOR ACTIVATED RECEPTOR MODULATORS

This application is a United States national phase entry, pursuant to 35 U.S.C. 371, of PCT/US2004/038232, filed on Dec. 8, 2004, which claims the benefit of U.S. provisional patent application Ser. No. 60/550,636, filed Mar. 5, 2004, and hereby incorporated by reference in their entirety.

FIELD OF THE INVENTION

The present invention relates to a compound of selective peroxisome proliferator activated receptor modulator (SP-PARM), more specifically a compound of PPAR gamma partial agonist, which is useful for the treatment and/or prevention of disorders modulated by a PPAR.

BACKGROUND OF THE INVENTION

The peroxisome proliferator activated receptors (PPARs) are members of the nuclear receptor gene family that are activated by fatty acids and fatty acid metabolites. The PPARs belong to the subset of nuclear receptors that function as heterodimers with the 9-cis retinoic acid receptor (RXR). Three subtypes, which are designated as PPARα, PPARγ and PPARδ are found in species ranging from *Xenopus* to humans.

PPARα is the main subtype in the liver and has facilitated analysis of the mechanism by which peroxisome proliferators exert their pleiotropic effects. PPARα is activated by a number of medium and long-chain fatty acids, and it is involved in stimulating β-oxidation of fatty acids. PPARα is also involved with the activity of fibrates and fatty acids in rodents and humans. Fibric acid derivatives such as clofibrate, fenofibrate, bezafibrate, ciprofibrate, beclofibrate and etofibrate, as well as gemfibrozil, produce a substantial reduction in plasma triglycerides along with moderate reduction in low-density lipoprotein (LDL) cholesterol, and they are used particularly for the treatment of hypertriglyceridemia.

PPARγ is the main subtype in adipose tissue and involved in activating the program of adipocyte differentiation. PPARγ is not involved in stimulating peroxisome proliferation in the liver. There are two isomers of PPARγ:PPARγ1 and PPARγ2, which differ only in that PPARγ2 contains an additional 28 amino acids present at the amino terminus. The DNA sequences for the PPARγ receptors are described in Elbrecht, et al., BBRC 224; 431-437 (1996). Although peroxisome proliferators, including the fibrates and fatty acids, activate the transcriptional activity of PPAR's, only prostaglandin $J_2$ derivatives have been identified as natural ligands for PPARγ, which also binds the anti-diabetic agents thiazolidinediones with high affinity. The physiological functions of PPARα and PPARγ in lipid and carbohydrate metabolism were uncovered once it was recognized that they were the receptors for the fibrate and glitazone drugs, respectively.

PPARα and PPARγ receptors have been implicated in diabetes mellitus, cardiovascular disease, obesity, and gastrointestinal disease, such as inflammatory bowel disease and other inflammation related illnesses. Such inflammation related illnesses include, but are not limited to Alzheimer's disease, Crohn's disease, rheumatoid arthritis, psoriasis, and ischemia reprofusion injury. By contrast, PPARδ (also referred to as PPARβ and NUC1) is not reported to be receptor for any known class of drug molecules, and its role in mammalian physiology has remained undefined. The human nuclear receptor gene PPARδ (hPPARδ) has been cloned from a human osteosarcoma cell cDNA library and is fully described in A. Schmidt et al., *Molecular Endocrinology*, 6:1634-1641 (1992).

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes, which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL (known as the "bad" cholesterol) which are risk factors in cardiovascular diseases. The constellation of symptoms which includes hyperinsulemia combined with hypertension, elevated body weight, elevated triglycerides and elevated LDL is known as Syndrome X.

Hyperlipidemia is a condition which is characterized by an abnormal increase in serum lipids, such as cholesterol, triglycerides and phospholipids. These lipids do not circulate freely in solution in plasma, but are bound to proteins and transported as macromolecular complexes called lipoproteins. One form of hyperlipidemia is hypercholesterolemia, characterized by the existence of elevated LDL cholesterol levels. The initial treatment for hypercholesterolemia is often a diet low in fat and cholesterol coupled with appropriate physical exercise. Drug intervention is initiated if LDL-lowering goals are not met by diet and exercise alone. It is desirable to lower elevated levels of LDL cholesterol and increase levels of HDL cholesterol. Generally, it has been found that increased levels of HDL are associated with lower risk for coronary heart disease (CHD). See Gordon, et al., *Am. J. Med.*, 62, 707-714 (1977); Stampfer, et al., *N. England J. Med.*, 325, 373-381 (1991); and Kannel, et al., *Ann. Internal Med.*, 90, 85-91 (1979). An example of an HDL raising agent is nicotinic acid, but the quantities needed to achieve HDL elevation are associated with undesirable effects, such as flushing.

There are several treatments currently available for treating diabetes mellitus but these treatments still remain unsatisfactory and have limitations. While physical exercise and reduction in dietary intake of calories will improve the diabetic condition, compliance with this approach can be poor because of sedentary lifestyles and excess food consumption, in particular high fat-containing food. Therefore, treatment with hypoglycemics, such as sulfonylureas (e.g., chlorpropamide, tolbutamide, tolazamide and acetohexamide) and biguanides (e.g. phenformin and metformin) are often necessary as the disease progresses. Sulfonylureas stimulate the β cells of the pancreas to secrete more insulin as the disease progresses. However, the response of the β cells eventually fails and treatment with insulin injections is necessary. In addition, both sulfonylurea treatment and insulin injection have the life threatening side effect of hypoglycemic coma, and thus patients using these treatments must carefully control dosage.

It has been well established that improved glycemic control in patients with diabetes (Type I and Type II) is accompanied by decreased microvasclular complications (DCCT and UKPDS). Due to difficulty in maintaining adequate glycemic control over time in patients with Type II diabetes, the use of insulin sensitizers in the therapy of Type II diabetes is growing. There is also a growing body of evidence that PPARγ agonist, insulin sensitizer, may have benefits in the treatment of Type II diabetes beyond their effects in improving glycemic control.

In the last decade a class of compounds known as thiazolidinediones (TZD) (e.g. U.S. Pat. Nos. 5,089,514; 4,342,771; 4,367,234; 4,340,605; and 5,306,726) have emerged as effective antidiabetic agents that have been shown to increase the sensitivity of insulin sensitive tissues, such as skeletal muscle, liver and adipose, to insulin. Increasing insulin sensitivity rather than the amount of insulin in the blood reduces the likelihood of hypoglycemic coma. Although thiazolidinediones have been shown to increase insulin sensitivity by binding to PPARγ receptors, this treatment also produces unwanted side effects such as weight gain and edema and, for troglitazone, liver toxicity.

The PPARγ partial agonist activity may become a distinct advantage since a number of studies have shown that PPAR-γ partial agonists including selective PPAR modulators (SPPARMs) have improved side effect profiles compared to full agonists especially as it relates to weight gain and edema. See Rocchi S. et al., *Molecular Cell*, 8:737-747 (2001); Berger J P, et al. *Mol Endocrinol* 17:662-676 (2003); Shimaya A, et al., *Metabolism* 49:411-417 (2000); Chakrabarti R, et al., *Diabetes* 52 (Suppl. 1) p 601 (Abstract) (2003); Kawai T, et al., *Metabolism*, 48:1102-1107 (1999); and Wulff E, et al., *Diabetes* 52 (Suppl. 1) p 594 (abstract) (2003).

The compounds that are not TZDs have also been reported as PPAR modulators. Adams et al. (WO 97/28115, WO 97/28135 and U.S. Pat. No. 5,895,051) discloses acetylphenols, which are useful as antiobesity and antidiabetic compounds. Leibowitz et al., (WO 97/28149) discloses compounds which are PPARδ agonists and useful for treating cardiovascular diseases and related conditions. Brooks et al. (WO 02/100813) discloses compounds of PPAR modulators that are useful for treating type II diabetes and other PPAR-mediated diseases and conditions. Ferritto Crespo et al., (WO 2004/000789) discloses compound of amide linker PPAR modulators.

In view of the above, an objective of the present invention is to provide new pharmaceutical agents which modulate PPAR receptors to prevent, treat and/or alleviate these diseases or conditions while diminishing one or more of the unwanted side effects associated with the current treatments.

SUMMARY OF THE INVENTION

An embodiment of the present invention is a compound of selective peroxisome proliferator activated receptor modulator (SPPARM) or a compound having the PPARγ partial agonist activity, which has a structural formula I,

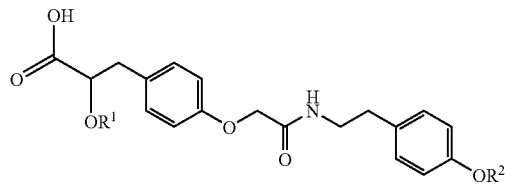

or a pharmaceutically acceptable salt, solvate, hydrate or stereoisomer thereof, wherein:
$R^1$ and $R^2$ are each independently: methyl or ethyl.

The compounds of the present invention are useful in the treatment and/or prevention of diseases or condition relates to hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component.

In one embodiment, the present invention also relates to a pharmaceutical composition comprising a compound of the present invention, or a pharmaceutically acceptable salt, solvate or hydrate thereof and a pharmaceutically acceptable carrier. Within the scope of this invention also include a pharmaceutical composition containing additional therapeutic agent as well as a compound of the present invention, or a pharmaceutically acceptable salt, solvate or hydrate thereof and optionally a pharmaceutically acceptable carrier.

In another embodiment, the present invention relates to a method of modulating a PPAR by contacting the receptor with a compound of the present invention, and a pharmaceutically acceptable salt, solvate or hydrate thereof.

DETAILED DESCRIPTION OF THE INVENTION

The compounds of the present invention are directed to peroxisome proliferator activated receptor (PPAR) agonists. The compounds the present invention are related more specifically to a compound of selective peroxisome proliferator activated receptor modulator (SPPARM) or a compound having the PPARγ partial agonist activity, which is useful for the treatment and/or prevention of disorders modulated by a PPAR, such as Type II diabetes, hyperglycemia, dyslipidemia, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other related diseases.

An embodiment of the present invention is a compound of selective peroxisome proliferator activated receptor modulator (SPPARM) or a compound having the PPARγ partial agonist activity, which has a structural formula I,

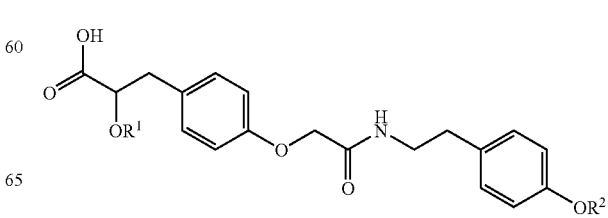

or a pharmaceutically acceptable salt, solvate, hydrate or stereoisomer thereof, wherein:

$R^1$ and $R^2$ are each independently: methyl or ethyl.

A preferred embodiment of the present invention is a compound having a structural formula II,

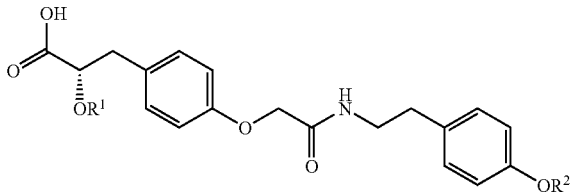

II or a pharmaceutically acceptable salt, solvate or hydrate thereof, wherein: $R^1$ and $R^2$ are each independently: methyl or ethyl.

Another preferred embodiment of the present invention is a compound of (2S)-3-(4-{[2-(4-methoxy-phenyl)-ethylcarbamoyl]-methoxy}-phenyl)-2-methoxy-propionic acid having a structural formula III,

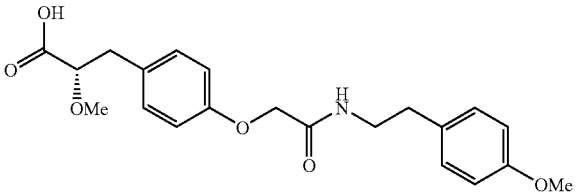

III or a pharmaceutically acceptable salt, solvate or hydrate thereof.

More preferred embodiment of the present invention is a compound of 3-(4-{[2-(4-ethoxy-phenyl)-ethylcarbamoyl]-methoxy}-phenyl)-2-methoxy-propionic acid having a structural formula IV,

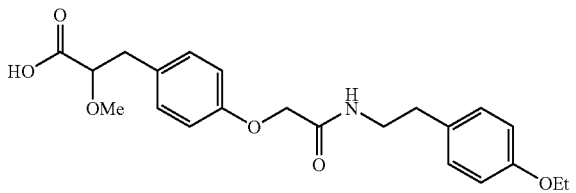

IV or a pharmaceutically acceptable salt, solvate or hydrate thereof.

Yet more preferred embodiment of the present invention is a compound of (S)-3-(4-{[2-(4-ethoxy-phenyl)-ethylcarbamoyl]-methoxy}-phenyl)-2-methoxy-propionic acid having a structural formula V,

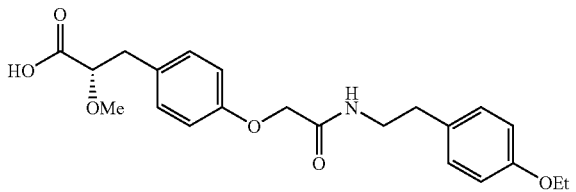

V or a pharmaceutically acceptable salt, solvate or hydrate thereof.

Also encompassed by the present invention is a pharmaceutical composition comprising a pharmaceutically acceptable carrier and a compound of the present invention or a pharmaceutically acceptable salt, solvate or hydrate thereof.

Also encompassed by the present invention a pharmaceutical composition comprising:

(1) a compound of the present invention, or a pharmaceutically acceptable salt, solvate, hydrate or stereoisomer thereof;

(2) a second therapeutic agent selected from the group consisting of: insulin sensitizers, sulfonylureas, biguanides, meglitinides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin; and (3) optionally a pharmaceutically acceptable carrier.

Also encompassed by the present invention a method of modulating a peroxisome proliferator activated receptor (PPAR) comprising the step of contacting the receptor with a compound of the present invention, or a pharmaceutically acceptable salt, solvate or hydrate thereof.

Also encompassed by the present invention is the method as recited above, wherein the PPAR is an alpha (α)-receptor.

Also encompassed by the present invention is the method as recited above wherein the PPAR is a gamma (γ)-receptor.

Also encompassed by the present invention is the method as recited above, wherein the PPAR is a alpha/gamma (α/γ)-receptor.

Also encompassed by the present invention is a method for treating and/or preventing a PPAR-γ mediated disease or condition in a mammal comprising the step of administering an effective amount of a compound of the present invention.

Also encompassed by the present invention is a method for treating and/or preventing a PPAR-α mediated disease or condition in a mammal comprising the step of administering an effective amount of a compound of the present invention.

Also encompassed by the present invention is a method for treating and/or preventing a PPAR-α/γ mediated disease or condition in a mammal comprising the step of administering an effective amount of a compound of the present invention.

Also encompassed by the present invention is a method for treating and/or preventing a disease or condition mediated by a PPAR-γ partial agonist in a mammal comprising the step of administering an effective amount of a compound of the present invention.

Also encompassed by the present invention is a method for lowering blood-glucose in a mammal comprising the step of administering an effective amount of a compound of the present invention.

Also encompassed by the present invention is a method of treating and/or preventing a disease or condition in a mammal selected from the group consisting of hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component, comprising the step of administering an effective amount of a compound of the present invention.

Also encompassed by the present invention is a method of treating and/or preventing diabetes mellitus in a mammal comprising the step of administering to a mammal a therapeutically effective amount of a compound of the present invention.

Also encompassed by the present invention is a method of treating and/or preventing cardiovascular disease in a mammal comprising the step of administering to a mammal a therapeutically effective amount of a compound of the present invention, or a pharmaceutically acceptable salt, solvate or hydrate thereof.

Also encompassed by the present invention is a method of treating and/or preventing syndrome X in a mammal, comprising the step of administering to the mammal a therapeutically effective amount of a compound of the present invention, or a pharmaceutically acceptable salt, solvate or hydrate thereof.

Also encompassed by the present invention is a method of treating and/or preventing a disease or condition in a mammal selected from the group consisting of hyperglycemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, cardiovascular disease and other diseases where insulin resistance is a component, comprising the step of administering an effective amount of a compound of the present invention; and an effective amount of second therapeutic agent selected from the group consisting of: insulin sensitizers, sulfonylureas, biguanides, meglitinides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin.

Also encompassed by the present invention is use of a compound of the present invention, or a pharmaceutically acceptable salt, solvate or hydrate thereof, for the manufacture of a medicament for the treatment of a condition modulated by a PPAR.

Also encompassed by the present invention is use of a compound of the present invention, or a pharmaceutically acceptable salt, solvate or hydrate thereof, for the manufacture of a medicament for the treatment of diabetes.

The terms used to describe the present invention have the following meanings unless otherwise indicated.

The term "halo" refers to F, Cl, Br or I.

The term "active ingredient" means the compounds generically described by Formula I as well as the salts, solvates and prodrugs of such compounds.

The term "pharmaceutically acceptable" means that the carrier, diluents, excipients and salt must be compatible with the other ingredients of the composition, and not deleterious to the recipient thereof. Pharmaceutical compositions of the present invention are prepared by procedures known in the art using well-known and readily available ingredients.

"Preventing" refers to reducing the likelihood that the recipient will incur or develop any of the pathological conditions described herein.

"Treating" refers to mediating a disease or condition, and preventing or mitigating its further progression or ameliorating the symptoms associated with the disease or condition.

"Pharmaceutically-effective amount" means that amount of a compound of the present invention, or of its salt, solvate, hydrate or prodrug thereof that will elicit the biological or medical response of a tissue, system or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount, which is sufficient to modulate a PPAR receptor such as a PPARα, PPARγ or PPARα/γ receptor to mediate a disease or condition. Conditions mediated by PPAR receptors include, for example, diabetes mellitus, cardiovascular disease, Syndrome X, obesity and gastrointestinal disease. Additional conditions associated with the modulation of a PPAR receptor include inflammation related conditions, which include, for example, IBD (inflammatory bowel disease), rheumatoid arthritis, psoriasis, Alzheimer's disease, Chrohn's disease and ischemia reprofusion injury (stroke and miocardial infarction).

A "mammal" is an individual animal that is a member of the taxonomic class Mammalia. The class Mammalia includes humans, monkeys, chimpanzees, gorillas, cattle, swine, horses, sheep, dogs, cats, mice, rats and the like.

Administration to a human is most preferred. A human to whom the compounds and compositions of the present invention are administered has a disease or condition in which control blood glucose levels are not adequately controlled without medical intervention, but wherein there is endogenous insulin present in the human's blood. Non-insulin dependent diabetes mellitus (NIDDM) is a chronic disease or condition characterized by the presence of insulin in the blood, even at levels above normal, but resistance or lack of sensitivity to insulin action at the tissues.

Those skilled in the art will recognize that stereocenters exist in compound of the present invention. Accordingly, the present invention includes all possible stereoisomers and geometric isomers of the presently claimed compounds including racemic compounds and the optically active isomers.

The compounds of the present invention contain one or more chiral centers and exist in different optically active forms. When compounds of the present invention contain one chiral center, the compounds exist in two enantiomeric forms and the present invention includes both enantiomers and mixtures of enantiomers, such as racemic mixtures. Resolution of the final product, an intermediate or a starting material may be effected by any suitable method known in the art, for example by formation of diastereoisomeric salts which may be separated by crystallization; formation of diastereoisomeric derivatives or complexes which may be separated by crystallization and gas-liquid or liquid chromatography; selective reaction of one enantiomer with an enantiomer-specific reagent such as enzymatic esterification; and gas-liquid or liquid chromatography in a chiral environment such as on a chiral support, for example silica with a bound chiral ligand or in the presence of a chiral solvent. See also *Sterochemistry of Carbon Compounds* by E. L. Eliel (Mcgraw Hill, 1962) and *Tables of Resolving Agents* by S. H. Wilen. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the present invention has more than one chiral substituents, it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of the present invention may exist in different stable conformational forms, which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compound of the present invention may exist in zwitterionic form, and the present invention includes each zwitterionic form of compounds of formula I and mixtures thereof.

Certain compounds of the present invention and their salts may exist in more than one crystal form. Polymorphs of compounds of formula I form part of the present invention and may be prepared by crystallization of a compound of formula I under different conditions, such as using different solvents or different solvent mixtures for recrystallization; crystallization at different temperatures; and various modes of cooling ranging from very fast to very slow cooling during crystallization. Polymorphs may also be obtained by heating or melting a compound of formula I followed by gradual or fast cooling. The presence of polymorphs may be determined by solid probe NMR spectroscopy, IR spectroscopy, differential scanning calorimetry, powder X-ray diffraction or other available techniques.

Certain compounds of the present invention and their salts may exist in more than one crystal form, which includes each crystal form and mixtures thereof.

Certain compounds of the present invention and their salts may also exist in the form of solvates, for example hydrates, and thus the present invention includes each solvate and mixtures thereof.

"Pharmaceutically-acceptable salt" refers to salts of the compounds of formula I, which are substantially non-toxic to mammals. Typical pharmaceutically acceptable salts include those salts prepared by reaction of the compounds of the present invention with a mineral, organic acid: an organic base or inorganic base. Such salts are known as base addition salts, respectively. It should be recognized that the particular counterion forming a part of any salt of the present invention is not of a critical nature so long as the salt as a whole is pharmaceutically acceptable and the counterion does not contribute undesired qualities to the salt as a whole.

By virtue of its acidic moiety, a compound of the present invention forms salts with pharmaceutically acceptable bases. Some examples of base addition salts include metal salts such as aluminum; alkali metal salts such as lithium, sodium or potassium; and alkaline earth metal salts such as calcium, magnesium, ammonium, or substituted ammonium salts. Examples of substituted ammonium salts include, for instance, those with lower alkylamines such as trimethylamine and triethylamine; hydroxyalkylamines such as 2-hydroxyethylamine, bis-(2-hydroxyethyl)-amine or tri-(2-hydroxyethyl)-amine; cycloalkylamines such as bicyclohexylamine or dibenzylpiperidine, N-benzyl-β-phenethylamine, dehydroabietylamine, N,N'-bisdehydro-abietylamine, glucamine, N-piperazine methylglucamine; bases of the pyridine type such as pyridine, collidine, quinine or quinoline; and salts of basic amino acids such as lysine and arginine.

Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Compounds of the present invention, which are substituted with a basic group, may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid. These salts may be prepared by methods known to those skilled in the art.

Certain compounds of the present invention and their salts may also exist in the form of solvates, for example hydrates, and thus the present invention includes each solvate and mixtures thereof.

The compounds of present invention, which bind to and activate the PPARs, lower one or more of glucose, insulin, triglycerides, fatty acids and/or cholesterol, and are therefore useful for the treatment and/or prevention of hyperglycemia, dyslipidemia and in particular Type II diabetes as well as other diseases including syndrome X, Type I diabetes, hypertriglyceridemia, insulin resistance, diabetic dyslipidemia, hyperlipidemia, hypercholesteremia, heart failure, coagaulopathy, hypertension, and cardiovascular diseases, especially arteriosclerosis. In addition, these compounds are indicated to be useful for the regulation of appetite and food intake in subjects suffering from disorders such as obesity, anorexia bulimia and anorexia nervosa.

The compounds and compositions of the present invention are also useful to treat acute or transient disorders in insulin sensitivity, which sometimes occurs following a surgery, trauma, myocardial infarction and the like. The compounds and compositions of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who can benefit from administration of the compounds and compositions of the present invention.

The present invention further provides a method for the treatment and/or prophylaxis of hyperglycemia in a human or non-human mammal which comprises administering an effective, non-toxic amount of a compound of formula I, or a tautomeric form thereof and/or a pharmaceutically acceptable salt thereof and/or a pharmaceutically acceptable solvate thereof to a hyperglycemic human or non-human mammal in need thereof.

The compounds of the present invention are useful as therapeutic substances in preventing or treating Syndrome X, diabetes mellitus and related endocrine and cardiovascular disorders and diseases in human or non-human animals.

The present invention also relates to the use of a compound of formula I as described above for the manufacture of a medicament for treating a condition or disease mediated by PPARα, PPARγ, PPARγ-partial agonist or PPARα/γ dual agonist in a mammal.

A therapeutically effective amount of a compound of the present invention can be used for the preparation of a medicament useful for treating Syndrome X, diabetes, treating obesity, lowering tryglyceride levels, raising the plasma level of high density lipoprotein, and for treating, preventing or reducing the risk of developing arteriosclerosis, and for preventing or reducing the risk of having a first or subsequent atherosclerotic disease event in mammals, particularly in humans.

Additionally, an effective amount of a compound of the present invention and a therapeutically effective amount of one or more active agents selected from antihyperlipidemic agent, plasma HDL-raising agents, antihypercholesterolemic agents, fibrates, vitamins, aspirin, insulin secretogogues, insulin and the like can be used together for the preparation of a medicament useful for the above described treatments.

Advantageously, compositions containing the compound of the present invention or their salts may be provided in dosage unit form, preferably each dosage unit containing from about 1 to about 500 mg. It is understood that the amount of the compounds of the present invention that will be administered is determined by a physician considering of all the relevant circumstances.

Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially arteriosclerosis.

The compounds of the present invention may be used effectively alone or in combination with one or more additional active agents depending on the desired target therapy. Combination therapy includes administration of a single pharmaceutical dosage composition, which contains a compound of the present invention and one or more additional active agents, as well as administration of a compound of the present invention and each active agent in its own separate pharmaceutical dosage. For example, a compound of the present invention or thereof and an insulin secretogogue such as biguanides, meglitinides, thiazolidinediones, sulfonylureas, insulin or α-glucosidose inhibitors can be administered to the patient together in a single oral dosage composition such as a tablet or capsule, or each agent administered in separate oral dosages. Where separate dosages are used, a compound of the present invention and one or more additional active agents can be administered at essentially the same time, i.e., concurrently or at separately staggered times, i.e., sequentially; combination therapy is understood to include all these regimens.

An example of combination treatment or prevention of arteriosclerosis may involve administration of a compound of the present invention or salts thereof in combination with one or more of second active therapeutic agents: antihyperlipidemic agents; plasma HDL-raising agents; antihypercholesterolemic agents, fibrates, vitamins, aspirin and the like. As noted above, the compounds of the present invention can be administered in combination with more than one additional active agent.

Another example of combination therapy can be seen in treating diabetes and related disorders wherein the compounds of the present invention or salts thereof can be effectively used in combination with second active therapeutic, such as sulfonylureas, biguanides, meglitinides, thiazolidinediones, (X-glucosidase inhibitors, other insulin secretogogues, insulin as well as the active agents discussed above for treating arteriosclerosis.

The examples of second therapeutic agents are insulin sensitizers, PPARγ agonists, glitazones, troglitazone, pioglitazone, englitazone, MCC-555, BRL 49653, biguanides, metformin, phenformin, insulin, insulin minetics, sufonylureas, tolbutamide, glipizide, alpha-glucosidase inhibitors, acarbose, cholesterol lowering agent, HMG-CoA reductase inhibitors, lovastatin, simvastatin, pravastatin, fluvastatin, atrovastatin, rivastatin, other statins, sequestrates, cholestyramine, colestipol, dialkylaminoalkyl derivatives of a cross-linked dextran, nicotinyl alcohol, nicotinic acid: a nicotinic acid salt, PPARα agonists, fenofibric acid derivatives, gemfibrozil, clofibrate, fenofibrate, benzafibrate, inhibitors of cholesterol absorption, beta-sitosterol, acryl CoA:cholesterol acyltransferase inhibitors, melinamide, probucol, PPARδ agonists, antiobesity compounds, fenfluramine, dexfenfluramine, phentiramine, sulbitramine, orlistat, neuropeptide Y5 inhibitors, $\beta_3$ adrenergic receptor agonists, and ileal bile acid transporter inhibitors.

The compounds of the present invention and the pharmaceutically acceptable salts, solvates and hydrates thereof have valuable pharmacological properties and can be used in pharmaceutical compositions containing a therapeutically effective amount of a compound of the present invention, or pharmaceutically acceptable salts, esters or prodrugs thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper excipient is dependent upon the route of administration chosen. Pharmaceutical compositions typically contain from about 1 to about 99 weight percent of the active ingredient, which is a compound of the present invention.

Preferably, the pharmaceutical formulation is in unit dosage form. A "unit dosage form" is a physically discrete unit containing a unit dose suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts considering various factors, such as without limitation, the species, age, weight, sex, medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses of two, three or more times per day. Where delivery is via transdermal forms, administration is continuous.

Suitable routes of administration of pharmaceutical compositions of the present invention include, for example, oral, eye drop, rectal, transmucosal, topical or intestinal administration; parenteral delivery (bolus or infusion), including intramuscular, subcutaneous, intramedullary injections, as well as intrathecal, direct intraven-tricular, intravenous, intraperitoneal, intranasal, or intraocular injections. The compounds of the present invention can also be administered in a targeted drug delivery system, such as in a liposome coated with endothelial cell-specific antibody.

For oral administration, the compounds of the present invention can be formulated readily by combining the active compounds with pharmaceutically acceptable carriers well known in the art. Such carriers enable the compounds of the present invention to be formulated as tablets, pills, powders, sachets, granules, dragees, capsules, liquids, elixirs, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone, maize, starch, methyl cellulose, agar, bentonite, xanthan gum, alginic acid: or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid: sodium oleate, sodium benzoate, sodium acetate, sodium chloride, talc, and the like. When a dosage unit form is a capsule, it may contain, in addition to materials of the above type, a liquid carrier such as a fatty oil.

Solid forms include powders, tablets and capsules. A solid carrier can be one or more substances, which may also act as flavoring agents, lubricants, solubilisers, suspending agents, binders, tablet disintegrating agents and encapsulating material.

In powders, the carrier is a finely divided solid, which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquids include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration, the compounds of the present invention or salts thereof can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks' solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges Formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier, which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing for example up to 10% by weight of the active compound. The compounds of the present invention are preferably formulated prior to administration.

Biological Assays

Competitive Displacement Binding Assays

Binding assays are performed using scintillation proximity assay (SPA) technology, PPAR receptors, and corresponding radiolabeled ligands. PPARα and PPARγ along with their heterodimeric partner, retinoid X receptor α, are each produced using a baculovirus expression system. Biotinylated oligonucleotides containing PPAR response elements (PPREs) are used to couple the corresponding receptor dimers to yttrium silicate streptavidin-coated SPA beads. PPARγ- and PPARα-specific ligands are labeled with tritium and used in the appropriate corresponding assays. The $IC_{50}$ values (compound concentration which causes 50% inhibition) for each competing compound are calculated after deduction of non-specific binding (measured in the presence of 10 μM unlabeled ligand). Compounds are evaluated using an 11-point dose response curve with concentrations ranging from 0.169 nM to 10 μM. Reported values represent means from one to seven separate experiments.

Cotransfection (CTF) Assays

PPARγ or PPARα are constitutively expressed using plasmids containing the cytomegalovirus promoter. Reporter plasmids for the PPARγ CTF assays contain PPREs from the following genes: acyl coA oxidase (AOX); apolipoprotein A1 (ApoA1); lipoprotein lipase (LPL); or enoyl-CoA hydratase/3-hydroxyacyl-CoA dehydrogenase (HD) plus the thymidine kinase (TK) promoter upstream of the luciferase reporter cDNA. A PPARγ bacterial galactosidase (GAL4) chimeric system is also used. For PPARα, a GAL4 chimeric system is the standard CTF assay performed. All assays are done in CV-1 cells. Compounds are tested in full log dilution, from 0.1 nM to 10 μM in duplicate. Percent efficacies are determined relative to reference molecules with the efficacy value reflecting the greatest amount of agonist activity achieved in the CTF assay for each compound. Median effective concentration ($EC_{50}$) values are determined by computer fit to a concentration-response curve. An $EC_{50}$ value is not calculated if the efficacy for the compound is <20%. Reported values represent means from two to nine separate experiments.

Co-Factor Recruitment Assays

A mammalian-2-hybrid assay system in CTF format is done in CV-1 cells. The following plasmids are used: a mammalian expression vector encoding a fusion of the GAL4 DNA binding domain with the PPARγ ligand binding domain; a mammalian expression vector encoding a fusion of the VP16 transactivation domain with the nuclear receptor interaction domain of the respective co-activators: CREB-binding protein (CBP), peroxisome proliferator-activated receptor gamma coactivator-1 (PGC-1), activating signal cointegrator-2 (ASC-2), thyroid hormone receptor-activated protein complex (TRAP220), and the peptide C33; and a reporter plasmid (multimerized GAL4 binding sites/minimal TK promoter driving a luciferase cDNA). Cells are transfected in batch format and treated with compound (full log dilution from 0.1 nM to 10 μM) or vehicle for 24 hours. Subsequently, the cells are lysed and luciferase activity is measured. Luciferase activity serves as the endpoint for interaction between co-activator and receptor. The data are presented as % efficacy relative to a PPARγ full agonist and represent means from four to six separate experiments.

Evaluation of Glucose, Triglyceride and Hematocrit Levels and Body Weight Gain in Diabetic Mice Five-week-old male diabetic (db/db) mice (Harlan Laboratories, Indianapolis, Ind.) are housed in plastic cages (n=6/cage; cage size is approximately 10×20×8" with aspen chip bedding) with free access to water (sipper system—city tap water) and food (Purina 5008). After two weeks of acclimation, animals (7 weeks of age) are bled on day 0 at 1000-1200 h (lights on 0600 h) and assigned to treatment groups (n=5 or 6) based on starting glucose values. Compound or vehicle only treatments are administered daily by oral gavage at approximately 0730 h. Body weights are measured at the beginning (day 0) and end (day 7 or day 14) of the studies. Blood is collected in heparinized tubes from the tail of nonfasted animals two to three hours after the last dose. Hematocrit, glucose and triglycerides levels are then determined. The reported values for glucose and triglyceride levels represent the % of normalization compared to the lean littermate values set at 100% or glucose normalization calculated based on a normal glucose level of 250 mg/dl. Statistical significance between experimental groups is assessed using a two-sided student's t-test.

The following tables show the in-vitro data for the compound of present invention, (2S)-3-(4-{[2-(4-methoxy-phenyl)-ethylcarbamoyl]-methoxy}-phenyl)-2-methoxy-propionic acid having a structural formula III,

III

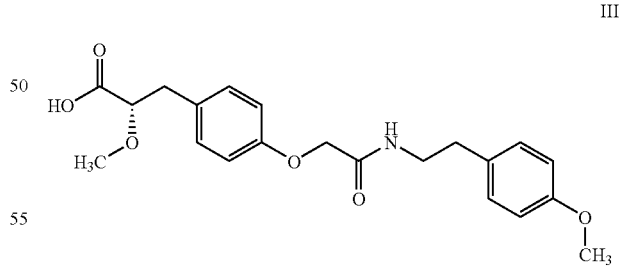

TABLE 1

| Binding and CTF Assays | | | | | |
|---|---|---|---|---|---|
| $IC_{50}$ (α) | $IC_{50}$ (γ) | Eff (α) | $EC_{50}$ (α) | Eff (γ) | $EC_{50}$ (γ) |
| 113 | 52 | 43 | 1305 | 60 | 1893 |

TABLE 2

Cofactor Recruitment Assays

| CBP Eff | CBP EC$_{50}$ | PGC1 Eff | PGC1 EC$_{50}$ | TRAP220 Eff | TRAP220 EC$_{50}$ | ASC2 Eff | ASC2 EC$_{50}$ | C33 Eff | C33 EC$_{50}$ |
|---|---|---|---|---|---|---|---|---|---|
| 15 | 1917 | 24 | 2065 | 7 | Eff < 20 | 15 | 1378 | 13 | 3013 |

TABLE 3

Response Element Assays

| Gla4 Eff | Gla4 EC$_{50}$ | HD Eff | HD EC$_{50}$ | LPL Eff | LPL EC$_{50}$ |
|---|---|---|---|---|---|
| 30 | 1977 | 54 | 1136 | 86 | 1419 |

IC$_{50}$ & EC$_{50}$ in nM; CTF (Eff) in % efficacy.

As shown in above tables, the compound of formula III is surprisingly a high affinity PPARγ partial agonist with PPARα activity. As seen in Table 1, this compound binds PPAR-γ with high affinity (IC$_{50}$=52 nM) and to PPARα with relatively lower affinity (IC$_{50}$=113). The compound of formula III has PPARγ partial agonist activity as demonstrated in co-transfection and co-factor recruitment assays. As seen in Tables 1 and 3, the PPARγ efficacy (% efficacy compared to a PPARγ full agonist set at 100%) achieved with this compound ranges from 30 to 86%. In addition, the ability of this compound to recruit specific co-factors to PPARγ ranges from 7 to 24% compared to a PPARγ full agonist (set at 100% recruitment: Table 2), thus making the compound of formula III a PPARγ partial agonist. The compound also demonstrates PPARα agonist activity as shown in table 1 (43% efficacy, 1305 nM EC$_{50}$).

To gain an understanding of the anti-diabetic efficacy and side effect profile of compound of formula III, diabetic (db/db) mice are administered compound of formula III at 1, 3, 10, and 30 mg/kg/day daily for 14 days by oral gavage. Plasma glucose and hematocrit levels along with body weight are measured before the study began (day 0) and at the end of the study (day 14). Compound of formula III displays excellent anti-diabetic efficacy reducing plasma glucose levels at all doses examined (42.7, 68.3, 96.1, and 109.3% normalization). Surprisingly, a dose-dependent reduction in hematocrit levels, indicative of plasma volume expansion, is not seen following administration of compound of formula III. Because anti-diabetic efficacy along with the liability of plasma volume expansion are common features of PPARγ full agonists [Armstrong and King (2004), Mudaliar, et al (2003), Nesto et al, (2004)], our data suggest that compound of formula III could be an improved therapy for the treatment of type 2 diabetes compared to the currently marketed PPARγ agonists The following tables show the in-vitro data for the compound of present invention, (S)-3-(4-{[2-(4-ethoxy-phenyl)-ethylcarbamoyl]-methoxy}-phenyl)-2-methoxy-propionic acid having a structural formula V,

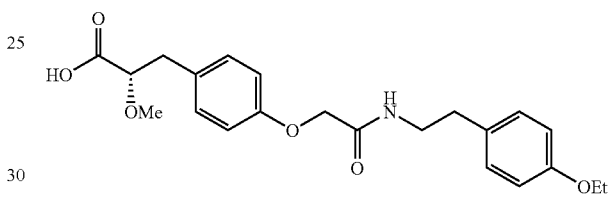

TABLE 1

Binding and CTF Assays

| IC$_{50}$ (α) | IC$_{50}$ (γ) | Eff (α) | EC$_{50}$ (α) | Eff (γ) | EC$_{50}$ (γ) |
|---|---|---|---|---|---|
| 360 | 30 | 39 | 1814 | 60 | 1012 |

TABLE 2

Cofactor Recruitment Assays

| CBP Eff | CBP EC$_{50}$ | PGC1 Eff | PGC1 EC$_{50}$ | TRAP220 Eff | TRAP220 EC$_{50}$ | ASC2 Eff | ASC2 EC$_{50}$ | C33 Eff | C33 EC$_{50}$ |
|---|---|---|---|---|---|---|---|---|---|
| 18 | 2638 | 24 | 2597 | 16 | 3063 | 33 | 2868 | 43 | 2893 |

TABLE 3

Response Element Assays

| Gla4 Eff | Gla4 EC$_{50}$ | HD Eff | HD EC$_{50}$ | LPL Eff | LPL EC$_{50}$ | ApoA1 Eff | ApoA1 EC$_{50}$ |
|---|---|---|---|---|---|---|---|
| 39 | 1907 | 58 | 1041 | 80 | 466 | 39 | 335 |

IC$_{50}$ & EC$_{50}$ in nM;
CTF (Eff) in % efficacy

As shown in above tables, the compound of formula V is surprisingly a high affinity PPARγ partial agonist with PPARα activity. As seen in Table 1, this compound binds PPARγ with high affinity ($IC_{50}$=30 nM) and to PPARα with relatively lower affinity ($IC_{50}$=360). The compound of formula V has PPARγ partial agonist activity as demonstrated in co-transfection and co-factor recruitment assays. As seen in Tables 1 and 3, the PPARγ efficacy (% efficacy compared to a PPARγ full agonist set at 100%) achieved with this compound ranges from 39 to 80%. In addition, the ability of this compound to recruit specific co-factors to PPARγ ranges from 16 to 43% compared to a PPARγ full agonist (set at 100% recruitment: Table 2), thus making the compound of formula V a PPARγ partial agonist. The compound also demonstrates PPARα agonist activity as shown in table 1 (39% efficacy, 1814 nM $EC_{50}$).

To gain an understanding of the anti-diabetic efficacy and side effect profile of compound of formula V, diabetic (db/db) mice and their lean littermates (db?/+) are administered compound of formula V at 3, 10, 30, and 100 mg/kg/day daily for 7 days by oral gavage. Plasma glucose, triglyceride, and hematocrit levels along with body weight are measured before the study began (day 0) and at the end of the study (day 7). Compound of formula V displayed excellent anti-diabetic efficacy significantly reducing plasma glucose and triglycerides levels at all doses examined (glucose: 61.2, 87.5, 105.6, 110.3% normalization; triglycerides: 108.1, 108.1, 121.1, 130.6% normalization). Unexpectedly, treatment with compound of formula V shows no statistically significant change in body weight gain or hematocrit levels at any dose administered. Because the anti-diabetic efficacy of PPARγ full agonists are known to be accompanied by significant weight gain and plasma volume expansion, the data herein indicates that compound of formula V could provide an improved therapy for the treatment of type 2 diabetes compared to the currently marketed or available PPARγ agonists.

The reaction scheme shown below generally illustrates a synthetic route to prepare the compounds of the present invention. The detailed examples are provided below.

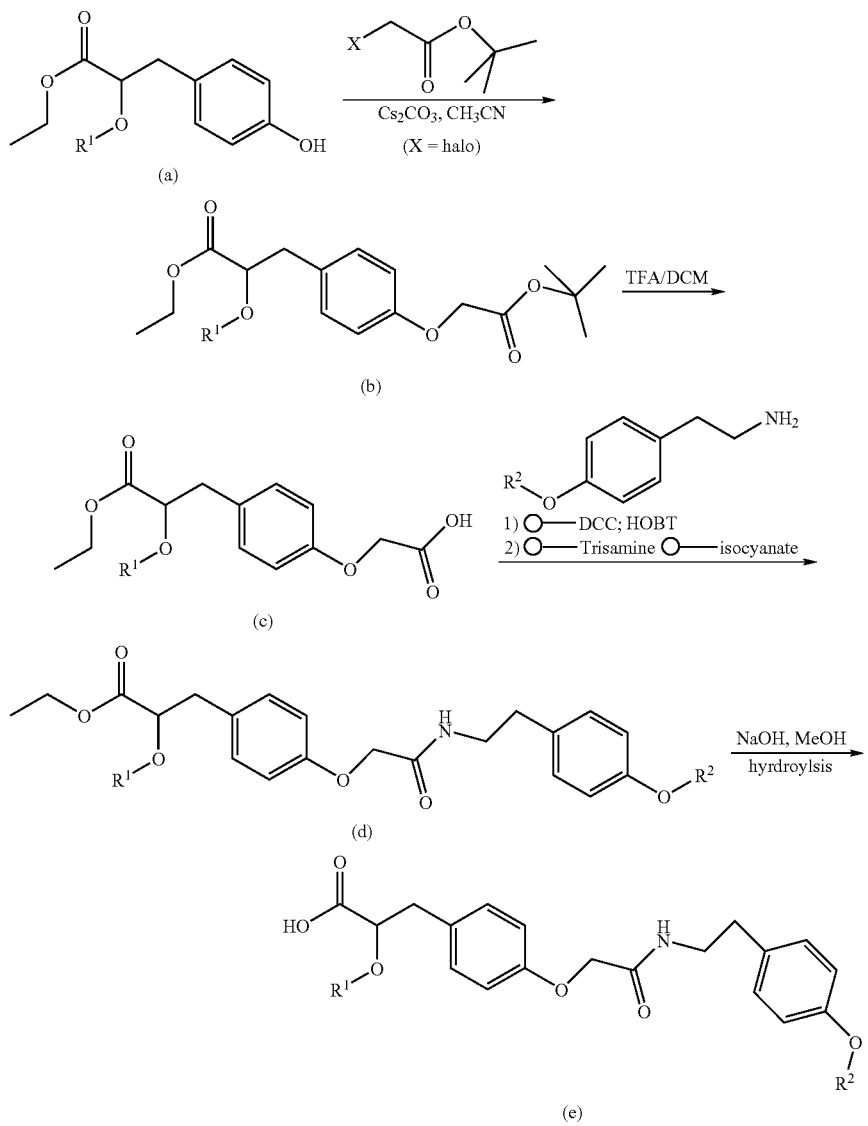

EXAMPLE 1

(2S)-3-(4-{[2-(4-methoxy-phenyl)-ethylcarbamoyl]-methoxy}-phenyl)-2-methoxy-propionic acid

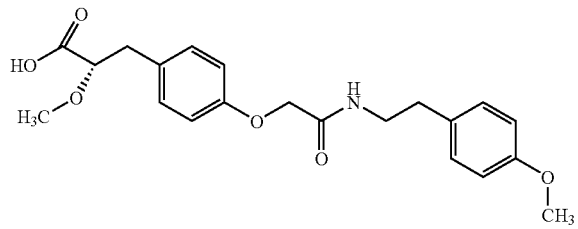

Step 1: Synthesis of Compound (b)

Compound (a) is dissolved in acetonitrile (0.1M) and treated with 2 eq of 2-bromo-2-methyl-propionic tert-butyl ester and 2.5 eq of cesium carbonate. The reaction is stirred at 80° C. for about 24 hours, filtered, and concentrated. The crude product is purified by silica gel column chromatography (10% ethyl acetate/hexane).

Step 2: Synthesis of Compound (c)

Compound (b) obtained from Step 1 is dissolved in trifluoroacetic acid (TFA) and $CH_2Cl_2$ (1:1; 0.5M). The reaction is stirred for about 2 hours and concentrated. The crude product is used in the next step.

Reaction Scheme

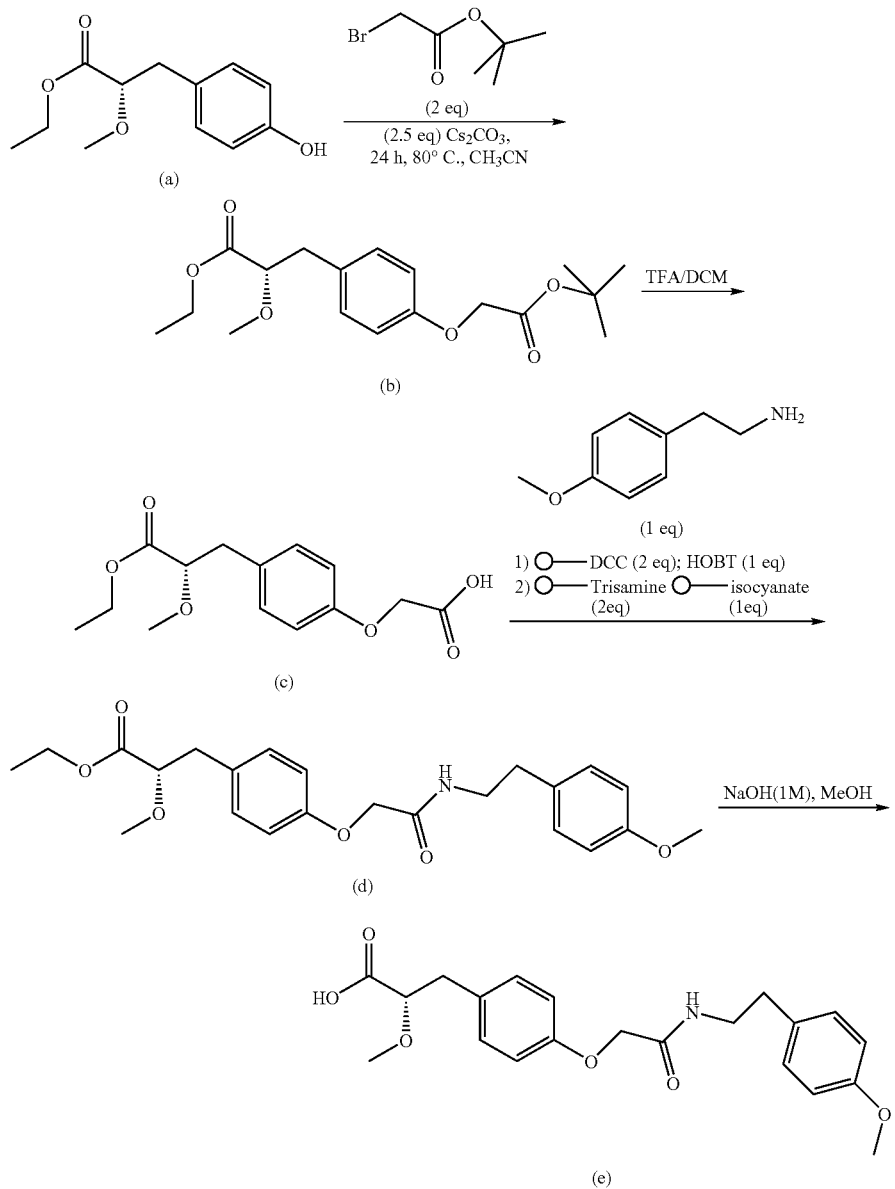

Step 3: Synthesis of Compound (d)

Compound (c) obtained from Step 2 is dissolved in dichloromethane (DCM) and treated with 2 eq of PS-carbodiimide and 1 eq of HOBT followed by 1.1 eq of 2-(4-ethoxy-phenyl)-ethylamine. The reaction is stirred at room temperature using orbital stirring for about 10 hours. The supported reagent is filtered and washed twice with DCM. The crude product is dissolved in DCM, and PS-trisamine (2 eq) and PS-isocyanate (1 eq) are added. The reaction is stirred at room temperature for 2 hours under orbital stirring. The supported scavengers are filtered and washed twice with DCM. The solvent is removed, and the crude is used in the hydrolysis step.

Step 4: Synthesis of Compound (e)

Compound (d) obtained from Step 3 is dissolved in MeOH and treated with 10 eq 1M aqueous NaOH solution. The reaction is stirred at room temperature until the hydrolysis is completed by HPLC analysis. 1M HCl (1M in water) is added (until pH=3), and the solvent is removed under vacuum. The residue is diluted in $CH_2Cl_2/H_2O$ and filtered through a ChemElute cartridge. The eluent is concentrated and purified by HPLC-MS to give the title compound as a white solid. MS (ES) for $C_{21}H_{25}NO_6$ [M-H]$^+$: 386; melting point 97-98° C.

EXAMPLE 2

(R) and (S)-3-(4-hydroxy-phenyl)-2-methoxy-propionic acid sodium salt

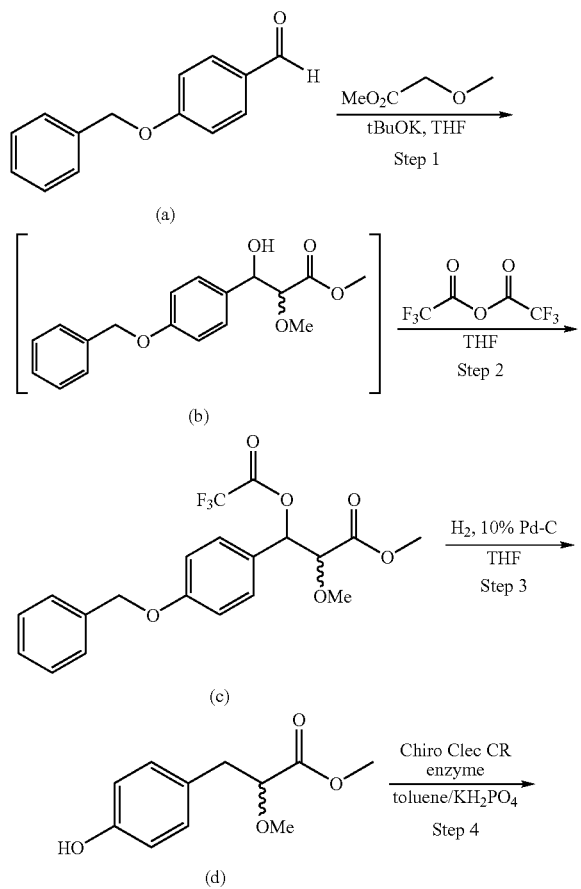

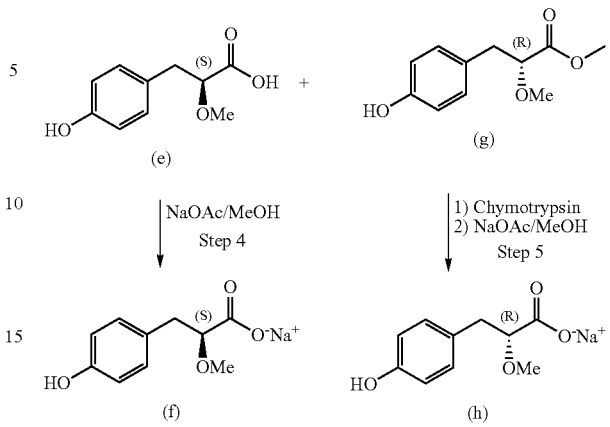

Step 1, 2, & 3: Synthesis of Compound (d)

(+/−)-3-(4-Hydroxy-phenyl)-2-methoxy-propionic acid methyl ester

Potassium tert-butoxide (1.6 M in tetrahydrofuran, 1163 mL, 1.86 moles) is cooled in a dry ice/acetone bath to −40° C. under nitrogen. A mixture of 4-benzyloxybenzaldehyde (358.9 g, 1.69 mole) and methylmethoxy acetate (184.3 mL, 1.86 mole) in tetrahydrofuran (1076 mL) is added over 30 to 60 min. The reaction is stirred at −40° C. for about 1 to 2 h to obtain intermediate (b). To intermediate (b) is added a solution of trifluoroacetic anhydride (710.3 g, 3.38 mole) in tetrahydrofuran (1600 mL) slowly over 25 min, and the reaction allowed to warm no greater than 15° C. The reaction is stirred overnight to provide compound (c).

Palladium on carbon (5%, 125.4 g) is suspended in tetrahydrofuran (500 mL). The reaction mixture containing compound (c) (about 4500 mL) is added and rinsed with tetrahydrofuran (1000 mL). The reaction is placed under hydrogen on a Parr shaker at 25 psig at room temperature. The reaction is hydrogenated for 26 h at about 19-32° C. The mixture is filtered over Hyflo Supercel® and the Parr shaker rinsed with tetrahydrofuran (2000 mL). The organic solution is concentrated in vacuo to the lowest possible volume. Toluene (2500 mL) is added, and the solution washed carefully with 10% $NaHCO_3$ (280 g in 2800 mL water). The layers are separated, and the organic phase is washed with water (2800 mL). The organic phase is concentrated its vacuo to provide about 271.8 g (76%) of compound (d), (+/−)-3-(4-hydroxy-phenyl)-2-methoxy-propionic acid methyl ester, as an oil.

Step 4: Synthesis of Compound (f)

(S)-3-(4-hydroxy-phenyl)-2-methoxy-propionic acid sodium salt

A solution of 0.75 M $KH_2PO_4$ is adjusted to pH=7.4-7.8 with 5 M NaOH. Chiro CLEC CR enzyme is added with moderate agitation followed by addition of compound (d) (10.0 g, 47.6 mmol) in toluene (100 mL). The enzymatic hydrolysis is carried out at room temperature, and 1 M NaOH is added as needed to maintain a pH above 6.5. The hydrolysis is stopped when the concentration of the aqueous layer indicates the conversion is at 35-42%, generally within about 4-36 h, depending on the activity of the enzyme. (See HPLC conditions below). The enzyme is filtered from the solution and rinsed with $KH_2PO_4$ buffer solution (1-2 mL). The organic and aqueous phases are separated. The aqueous portion is adjusted to pH=1.9-2.1 with 4 M HCl while maintaining the temperature at 20-25° C. The aqueous portion is extracted with isopropyl acetate. The layers are separated. The volume of the isopropyl acetate portion is measured, and the concentration of compound (e) is calculated. The isopropyl acetate phase is concentrated in vacuo to 70-80 mg/ml. The volume is measured, and the moles of compound (e) are calculated prior to crystallization. At room temperature and with moderate agitation, sodium acetate dissolved in methanol (11% wt/vol) is added to the isopropyl acetate solution of compound (e) such that a molar ratio of sodium acetate to compound (e) of 1.3 is achieved. Haziness and crystal formation is observed within 5-10 min. If not, the solution is seeded with compound (f). When haziness and crystal formation is evident, the agitation speed is slowed and stirring continued for 12 h at room temperature. The crystals are filtered and washed with room temperature isopropyl acetate (15 mL) and dried under vacuum at 45° C. to obtain compound (f) (3.1-3.6 g), (s)-3-(4-hydroxy-phenyl)-2-methoxy-propionic acid sodium salt. If chiral ee assay indicates ee <97%, the material is reslurried/recrystallized with 15 volumes of 99% vol/vol solution of isopropanol/water at reflux.

HPLC conditions: Column: Zorbax RX C-8, 4.6 mm×25 cm; Mobile Phase: 70% 0.1% $H_3PO_4$/30% Acetonitrile; Flow: 1 ml/min; Wavelength: 230 nm; Temp: ambient; Retention Times: compound (e)=4.3-4.6 min, compound (d)=9.3-9.7 min, isopropyl acetate=9.9-10.3, toluene: approx 50 min.

Step 5: Synthesis of Compound (h)

(R)-3-(4-hydroxy-phenyl)-2-methoxy-propionic acid sodium salt

The organic layer from the enzymatic hydrolysis (Step 4), containing compound (g), is concentrated to an oil. The concentration of (R)-3-(4-hydroxy-phenyl)-2-methoxy-propionic acid methyl ester contained in the oil is determined to be 0.40 g/g oil by HPLC, and the total amount of substrate is calculated. The oil containing (R)-3-(4-hydroxy-phenyl)-2-methoxy-propionic acid methyl ester (1399 g, 6.65 mol, corrected for concentration) is washed by combining with tert-butyl methyl ether (11520 mL, 8.2 vol), water (5120 mL, 3.6 vol) and 0.75 M $KH_2PO_4$ buffer (2560 mL, 1.8 vol) that has been pH adjusted to 7.5 with 5 N NaOH. The resulting organic layer is then taken into the hydrolysis reaction by adding 0.75 M $KH_2PO_4$ buffer (11560 mL, 8.3 vol) that has been pH adjusted to 7.5 with 5 N NaOH and chymotrypsin (25.6 g, 1.8 wt %). The reaction mixture is then stirred at 20-25° C. for 49 h with fast agitation while not allowing any contact between the agitator blade and the flask wall to minimize enzyme destruction. The product solution is filtered over Hyflo Supercel® and the filter aid cake is washed with 0.75 M $KH_2PO_4$ buffer (1280 mL, 0.9 vol) that has been pH adjusted to 7.5 with 5 N NaOH. Additional tert-butyl methyl ether (1280 mL, 0.9 vol) is added to the product solution to make the separation between the organic and aqueous phases more distinct. The aqueous phase is separated from the organic phase and then lowered to pH=2.0 with 4 N HCl (3000 mL, 2.1 vol). The aqueous portion is filtered over Hyflo Supercel® to remove particulate matter from the enzyme and the filter aid cake washed with 0.75 M $KH_2PO_4$ buffer (1280 mL, 0.9 vol) that has been pH adjusted to 7.5 with 5 N NaOH. The product is extracted from the aqueous portion with isopropyl acetate (46800 mL, 33.4 vol) and the volume of isopropyl acetate is then concentrated to 4.65 vol (6500 mL) via vacuum distillation (45° C./25"Hg). A mixture of sodium acetate (258.5 g, 3.1 mol) in methanol (2176 mL, 1.6 vol) is added to the product solution over 15 min at 20-25° C. The cloudy solution is seeded with compound (h), stirred at 20-25° C. for 9-10 h and filtered. The solid is washed with isopropyl acetate (1280 mL, 0.9 vol), collected and dried in a vacuum oven at 45° C. overnight to provide compound (h) (521.69 g), (R)-3-(4-hydroxy-phenyl)-2-methoxy-propionic acid sodium salt, as a white solid with ee=97.8%.

EXAMPLE 3

(R)-3-(4-{[2-(4-Ethoxy-phenyl)-ethylcarbamoyl]-methoxy}-phenyl)-2-methoxy-propionic acid

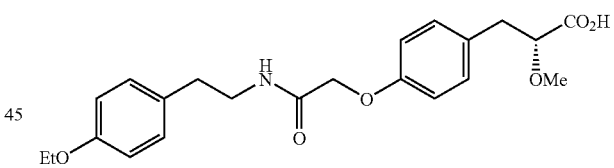

Reaction Scheme

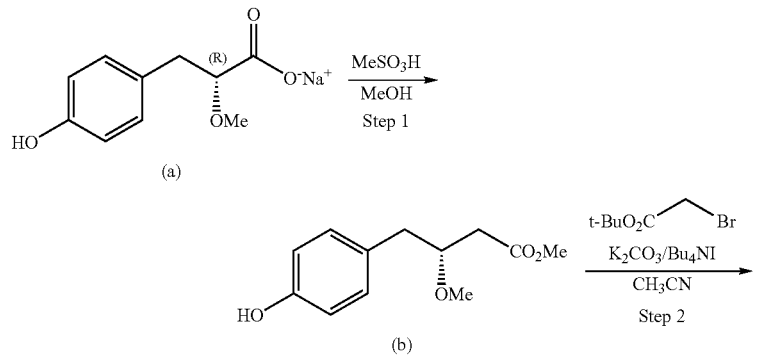

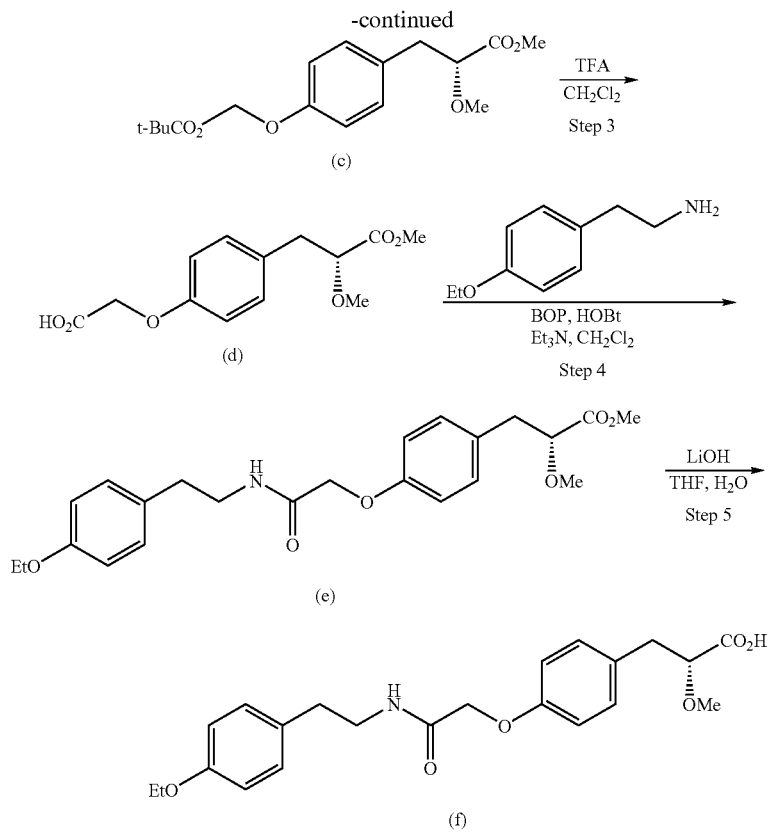

Step 1: Synthesis of Compound (b)

(R)-3-(4-Hydroxy-phenyl)-2-methoxy-propionic acid methyl ester

Compound (a), (R)-3-(4-hydroxy-phenyl)-2-methoxy-propionic acid sodium salt, (Example 2, Step 5) (5.00 g, 22.9 mmol) is dissolved in methanol (125 mL) and treated with methanesulfonic acid (7.44 mL, 114.6 mmol). The reaction is stirred at room temperature for 1 h. The reaction is concentrated in vacuo and the resulting residue taken up in diethyl ether. The organic portion is washed with water (2×) and saturated NaHCO$_3$ solution, dried (Na$_2$SO$_4$), filtered and concentrated in vacuo to yield 4.00 g (83%) of an off-white solid. The material is used without further purification. $^1$H NMR (400 MHz, CDCl$_3$) δ 7.06 (dd, J=2.2, 6.4 Hz, 2H), 6.72 (dd, J=2.2, 6.4 Hz, 2H), 5.38 (bd s, 1H), 3.95 (dd, J=5.3, 7.1 Hz, 1H), 3.71 (s, 3H), 3.35 (s, 3H), 2.95 (m, 2H); MS (electrospray), 209.2 (ES−).

Step 2: Synthesis of Compound (c)

(R)-3-(4-tert-Butoxycarbonylmethoxy-phenyl)-2-methoxy-propionic acid methyl ester Compound (b) (5.4 g, 25.69 mmol), obtained from Step 1, is dissolved in acetonitrile (50 mL) and treated with tert-butyl bromoacetate (5.01 g, 25.69 mmol), K$_2$CO$_3$ (7.10 g, 51.37 mmol) and tetrabutylammonium iodide (0.95 g, 2.57 mmol) and heated to 70° C. while rapidly stirring for 3 h. The reaction is filtered, rinsed with acetonitrile, and concentrated in vacuo. The resulting residue is taken up in ethyl acetate and washed sequentially with water, saturated NaHCO$_3$ solution, water, and brine. The organic phase is dried (Na$_2$SO$_4$), filtered, and concentrated in vacuo to yield 8.5 g, which is used without further purification. $^1$H NMR (400 MHz, CDCl$_3$) 8.7.12 (d, J=8.8 Hz, 2H), 6.81 (d, J=8.3 Hz, 2H), 4.48 (s, 2H), 3.92 (m, 1H), 3.70 (s, 3H), 3.34 (s, 3H), 2.95 (m, 2H), 1.48 (s, 9H).

Step 3: Synthesis of Compound (d)

(R)-3-(4-Carboxymethoxy-phenyl)-2-methoxy-propionic acid methyl ester

Compound (c) (8.5 g, 26.20 mmol), obtained from Step 2, is dissolved in dichloromethane (190 mL)/trifluoroacetic acid (45 mL) and stirred at room temperature for 4 h. The reaction is concentrated in vacuo, and the resulting residue is dissolved in ethyl acetate. The organic phase is washed with water (3×). The product is extracted into saturated NaHCO$_3$ solution (3×). The layers are separated, and the aqueous portion is carefully acidified with 5 N HCl to about pH 3-4. The aqueous is extracted with ethyl acetate (3×), making sure the pH of the aqueous layer is still around 3-4 and adding more 5 N HCl if necessary. The combined organic portions are dried over Na$_2$SO$_4$, filtered and concentrated in vacuo to yield 6.75 g (96%) of a white solid, which is used without further purification. $^1$H NMR (400 MHz, CDCl$_3$) δ 9.5 (bd s, 1H), 7.15 (d, J=8.7 Hz, 2H), 6.85 (d, J=8.8 Hz, 2H), 4.65 (s, 2H), 3.94 (dd, J=5.3, 7.9 Hz, 1H), 3.71 (s, 3H), 3.34 (s, 3H), 2.96 (m, 2H); MS (electrospray), 267.2 (ES−).

Step 4: Synthesis of Compound (e)

(R)-3-(4-{[2-(4-Ethoxy-phenyl)-ethylcarbamoyl]-methoxy}-phenyl)-2-methoxy-propionic acid methyl ester Method 1: Compound (d) (6.4 g, 23.85 mmol), obtained from Step 3, is dissolved in dichloromethane (150 mL) and treated with benzotriazol-1-yloxytris(dimethylamino) phosphonium hexafluorophosphate (BOP) (15.83 g, 35.78 mmol), hydroxybenzotriazole (4.84 g, 35.78 mmol), and triethylamine (6.66 mL, 47.71 mmol). The reaction is cooled in an ice bath and 2-(4-methoxyphenyl)ethylamine (4.34 g, 26.24 mmol) is added. The ice bath is removed, and the mixture is stirred at room temperature for about 18 h. The reaction is diluted with dichloromethane and washed sequentially with water (2×), 1 N HCl (2×), saturated NaHCO$_3$ solution, and brine. The organic portion is dried (Na$_2$SO$_4$), filtered, and concentrated in vacuo to yield 17 g of an orange oil. Purify the crude product by silica gel chromatography by eluting with 1:1 ethyl acetate/hexane to yield 9.0 g (91%) of a white solid. $^1$H NMR (400 MHz, CDCl$_3$) δ 7.15 (d, J=6.8 Hz, 2H), 7.04 (dd, J=1.8, 6.6 Hz, 2H), 6.80 (m, 4H), 6.60 (bd s, 1H), 4.43 (s, 2H), 4.01 (q, J=7.0 Hz, 2H), 3.94 (m, 1H), 3.72 (s, 3H), 3.56 (q, J=6.5 Hz, 2H), 3.34 (s, 3H), 2.99-2.95 (m, 2H), 2.76 (t, J=7.0 Hz, 2H), 1.41 (t, J=7.0 Hz, 3H).

Method 2: Compound (d) (1.0 eq) is dissolved in ethyl acetate under nitrogen. 1,1'-Carbonyldiimidazole (1.27 eq) is added, and the reaction is stirred at room temperature for 1 h. The reaction is cooled in an ice bath and 2-(4-methoxyphenyl)ethylamine (1.21 eq) is added slowly. The reaction is allowed to rise to room temperature with stirring overnight. The reaction is washed sequentially with 1 N HCl, saturated NaHCO$_3$ solution, and water. The organic portion is concentrated in vacuo. The resulting residue is redissolved in tetrahydrofuran. The solution is concentrated in vacuo to remove ethyl acetate and provide a solid (93%). If necessary, the material is purified as described in Method 1.

Step 5: Synthesis of Compound (f)

(R)-3-(4-{[2-(4-Ethoxy-phenyl)-ethylcarbamoyl]-methoxy}-phenyl)-2-methoxy-propionic acid Compound (e) (14.0 g, 33.70 mmol), obtained from Step 4, is dissolved in tetrahydrofuran (240 mL) and cooled in an ice bath. Lithium hydroxide (1.61 g, 67.39 mmol) in water (95 mL) is added and the reaction allowed to stir at room temperature for about 2 h. The tetrahydrofuran is removed in vacuo, diethyl ether is added and the aqueous portion is extracted. The layers are separated, and the aqueous layer is extracted with more diethyl ether. The aqueous layer is separated and carefully acidified with 1 N HCl. The resulting white precipitate is filtered and taken up in dichloromethane. The solution is dried (Na$_2$SO$_4$), filtered, and concentrated in vacuo to yield 12.4 g (92%). $^1$H NMR (400 MHz, CDCl$_3$) δ 7.18 (dd, J=1.7, 6.5 Hz, 2H), 7.04 (dd, J=1.7, 6.5 Hz, 2H), 6.81 (m, 4H), 6.66 (bd m, 1H), 4.42 (s, 2H), 4.0 (m, 3H), 3.55 (q, J=7.0 Hz, 2H), 3.40 (s, 3H), 3.10 (m, 1H), 3.01 (m, 1H), 2.16 (t, J=7.0 Hz, 2H), 1.40 (t, J=7.0 Hz, 3H). $^1$H NMR (400 MHz, DMSO-d$_6$) δ 12.68 (s, 1H), 8.04 (bd t, J=5.7 Hz, 1H), 7.11 (dd, J=1.7, 6.5 Hz, 2H), 7.07 (dd, J=1.7, 6.5 Hz, 2H), 6.81 (m, 4H), 4.38 (s, 2H), 3.95 (q, J=7.0 Hz, 2H), 3.87 (q, J=4.8 Hz, 1H), 3.30 (m, 3H), 3.20 (s, 3H), 2.88 (m, 1H), 2.81 (m, 1H), 2.65 (t, J=7.0 Hz, 2H), 1.31 (t, J=7.0 Hz, 3H). LCMS—100% purity. Mass ion of 400.6 (ES−), and 402.5 (ES+).

ee=97.8%, retention time=6.71 min as determined by chiral HPLC under the following conditions: Column: 46×15 cm Chiralpak AD-H; Eluent: 50:50:0.1 isopropyl alcohol/heptane/trifluoroacetic acid; Flow: 0.6 ml/min; UV: 270 nm.

EXAMPLE 4

(S)-3-(4-{[2-(4-Ethoxy-phenyl)-ethylcarbamoyl]-methoxy}-phenyl)-2-methoxy-propionic acid

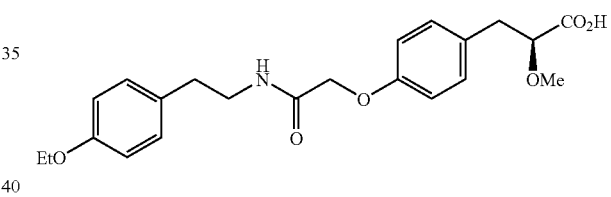

The title compound is prepared by essentialy following the procedures as described in Example 3 from (S)-3-(4-hydroxy-phenyl)-2-methoxy-propionic acid sodium salt. The following modifications are used as shown in reaction scheme below: toluene is used in Step 3 and Method 2 (Example 3, Step 4) is used in Step 4 with 1,1'-carbonyldiimidazole in ethyl acetate.

Reaction Scheme

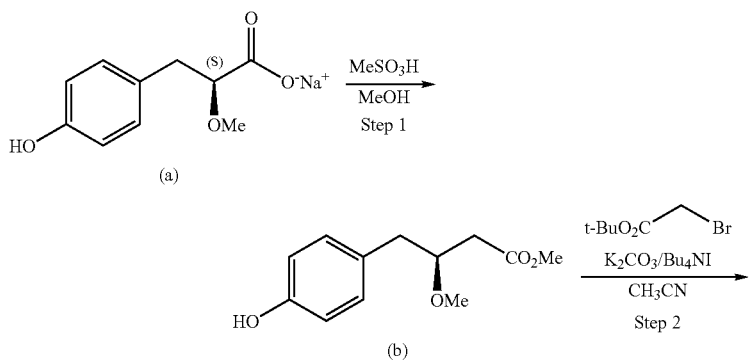

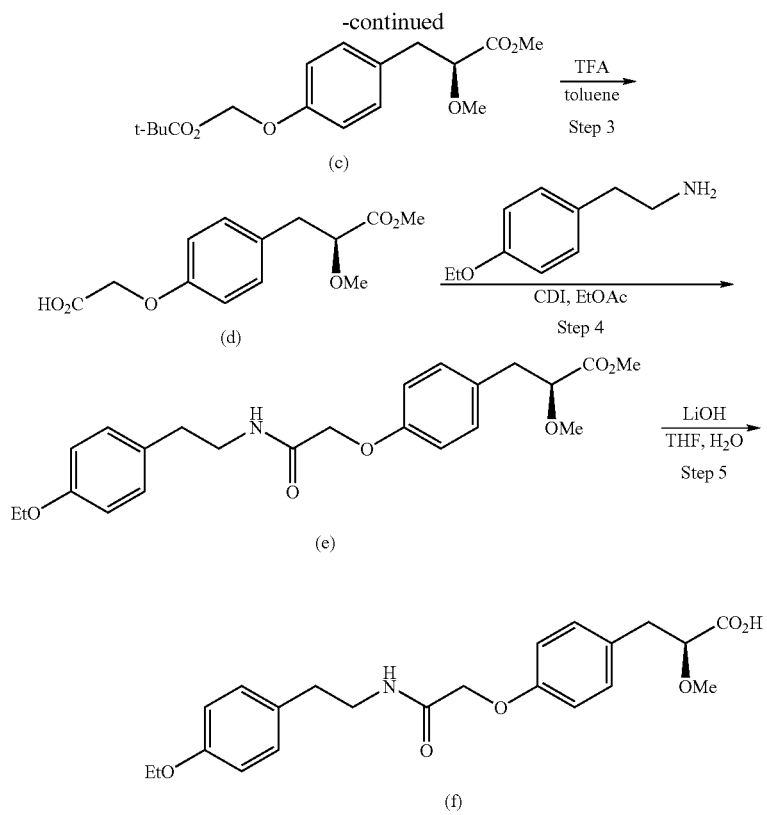

ee=98.0%, retention time=5.59 min as determined by chiral HPLC under the following conditions: Column: 46×15 cm Chiralpak AD-H; Eluent: 50:50:0.1 isopropyl alcohol/heptane/trifluoroacetic acid; Flow: 0.6 ml/min; UV: 270 nm.

Mass ion of 400.5 (ES−) and 402.4 (ES+); $^1$HNMR (CDCl$_3$) d 7.17 (d, J=8.6 Hz, 2H), 7.04 (d. J=8.6 Hz, 2H), 6.79 (m, 4H), 6.61 (bd m, 1H), 4.42 (s, 2H), 4.01 (m, 3H), 3.55 (q, J=6.6 Hz, 2H), 3.41 (s, 3H), 3.10 (dd, J=14.2, 4.6 Hz, 1H), 2.99 (dd, J=14.2, 6.9 Hz, 1H), 2.76 (t, J=6.9 Hz, 2H), 1.41 (t, J=6.9 Hz, 3H).

What is claimed is:

1. A compound having a structural formula I,

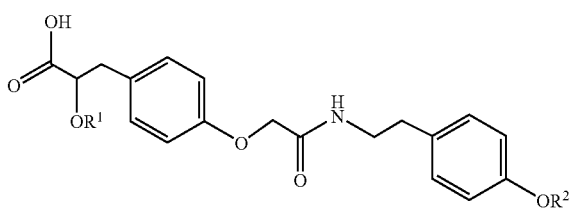

I or a pharmaceutically acceptable salt, or stereoisomer thereof, wherein:

$R^1$ and $R^2$ are each independently: methyl or ethyl.

2. The compound of claim 1, wherein the compound having a structural formula II,

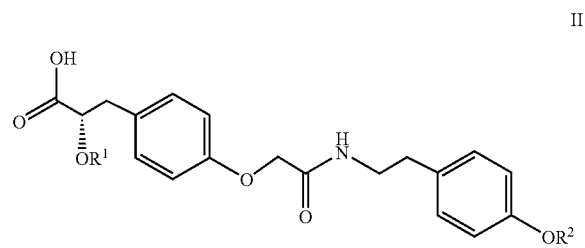

II or a pharmaceutically acceptable salt, solvate or hydrate thereof, wherein: $R^1$ and $R^2$ are each independently: methyl or ethyl.

3. The compound of claim 2, wherein the compound is (2S)-3-(4-{[2-(4-methoxy-phenyl)-ethylcarbamoyl]-methoxy}-phenyl)-2-methoxy-propionic acid having a structural formula III,

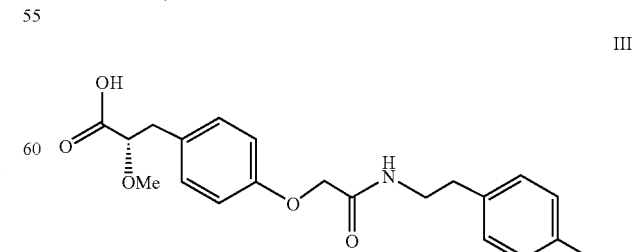

III or a pharmaceutically acceptable salt, solvate or hydrate thereof.

4. The compound of claim 1, wherein the compound is 3-(4-{[2-(4-ethoxy-phenyl)-ethylcarbamoyl]-methoxy}-phenyl)-2-methoxy-propionic acid having a structural formula IV,

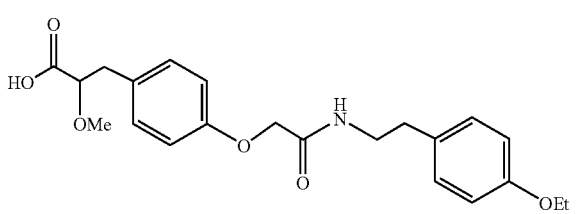

or a pharmaceutically acceptable salt, solvate or hydrate thereof.

5. The compound of claim 4, wherein the compound is (S)-3-(4-{[2-(4-ethoxy-phenyl)-ethylcarbamoyl]-methoxyl}-phenyl)-2-methoxy-propionic acid having a structural formula V,

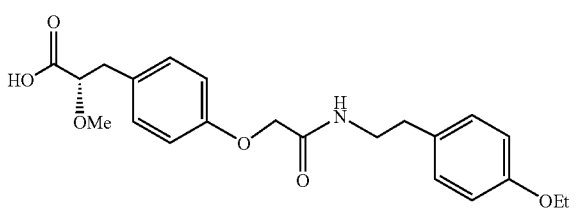

or a pharmaceutically acceptable salt, solvate or hydrate thereof.

6. A pharmaceutical composition comprising a pharmaceutically acceptable carrier and a compound of claims 1-5 or a pharmaceutically acceptable salt, or thereof.

7. A pharmaceutical composition comprising:
(1) a compound of claims 1-5, or a pharmaceutically acceptable salt, or stereoisomer thereof;
(2) a second therapeutic agent selected from the group consisting of: insulin sensitizers, sulfonylureas, biguanides, meglitinides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin; and
(3) optionally a pharmaceutically acceptable carrier.

8. A method for lowering blood-glucose in a mammal comprising the step of administering an effective amount of a compound of claims 1-5.

9. A method of treating disease or condition in a mammal selected from the group consisting of hyperglycemia, Type II diabetes, Type I diabetes, insulin resistance, comprising the step of administering an effective amount of a compound of claims 1-5.

10. A method of treating diabetes mellitus in a mammal comprising the step of administering to a mammal a therapeutically effective amount of a compound of claims 1-5.

11. A method of treating a disease or condition in a mammal selected from the group consisting of hyperglycemia, Type II diabetes, Type I diabetes, insulin resistance, comprising the step of administering an effective amount of a compound of claims 1-5; and an effective amount of second therapeutic agent selected from the group consisting of: insulin sensitizers, sulfonylureas, biguanides, meglitinides, thiazolidinediones, α-glucosidase inhibitors, insulin secretogogues, insulin, antihyperlipidemic agents, plasma HDL-raising agents, HMG-CoA reductase inhibitors, statins, acryl CoA:cholestrol acyltransferase inhibitors, antiobesity compounds, antihypercholesterolemic agents, fibrates, vitamins and aspirin.

* * * * *